(12) United States Patent
Sturm

(10) Patent No.: US 9,868,936 B2
(45) Date of Patent: Jan. 16, 2018

(54) CELL CULTURE METHOD

(71) Applicant: ISOPOGEN PTY LTD, Perth, WA (US)

(72) Inventor: Marian June Sturm, Samson (AU)

(73) Assignee: ISOPOGEN PTY LTD, Samson (AU)

( * ) Notice: Subject to any disclaimer, the term of this patent is extended or adjusted under 35 U.S.C. 154(b) by 0 days.

(21) Appl. No.: 14/443,652

(22) PCT Filed: Nov. 3, 2014

(86) PCT No.: PCT/AU2014/001031
§ 371 (c)(1),
(2) Date: May 18, 2015

(87) PCT Pub. No.: WO2015/061839
PCT Pub. Date: May 7, 2015

(65) Prior Publication Data
US 2015/0307844 A1   Oct. 29, 2015

(30) Foreign Application Priority Data
Nov. 4, 2013 (AU) .................................. 2013904257

(51) Int. Cl.
| | | |
|---|---|---|
| *C12N 5/077* | (2010.01) | |
| *A61K 35/28* | (2015.01) | |
| *C12N 5/0775* | (2010.01) | |
| *A61K 35/30* | (2015.01) | |
| *A61K 35/33* | (2015.01) | |
| *A61K 35/34* | (2015.01) | |
| *A61K 35/36* | (2015.01) | |
| *A61K 35/407* | (2015.01) | |

(52) U.S. Cl.
CPC ............ *C12N 5/0652* (2013.01); *A61K 35/28* (2013.01); *A61K 35/30* (2013.01); *A61K 35/33* (2013.01); *A61K 35/34* (2013.01); *A61K 35/36* (2013.01); *A61K 35/407* (2013.01); *C12N 5/0663* (2013.01); *C12N 2500/84* (2013.01)

(58) Field of Classification Search
CPC ....... C12N 5/0652; A61K 35/36; A61K 35/33
See application file for complete search history.

(56) References Cited

U.S. PATENT DOCUMENTS

| | | | | |
|---|---|---|---|---|
| 2005/0090002 A1* | 4/2005 | Cancedda | ............ | C12N 5/0655 435/366 |
| 2010/0272694 A1* | 10/2010 | Yang | .................... | A01N 1/0221 424/93.7 |

FOREIGN PATENT DOCUMENTS

WO   WO/2000/027996   5/2000

OTHER PUBLICATIONS

Herrmann et al. "Mesenchymal stromal cell therapy for steroid-refractory acute and chronic graft versus host disease: a phase 1 study" Int J Hematol (2012) 95:182-188.*
Le Blanc et al. "Mesenchymal stem cells for treatment of steroid-resistant, severe, acute graft-versus-host disease: a phase II study" Lancet. 2008; 371:1579-1586.*
International Search Report and Written Opinion for related PCT Application No. PCT/AU2014/001031 dated Dec. 24, 2014.
International Preliminary Examination Opinion for related PCT Application No. PCT/AU2014/001031 dated Apr. 17, 2015.
Spees, J.L. et al., "Internalized antigens must be removed to prepare hypoimmunogenic mesenchymal stem cells for cell and gene therapy", Molecular Therapy, 2004, vol. 9, No. 5, pp. 747-756.
Gregory, C.A. et al., "Enhanced engraftment of mesenchymal stem cells in a cutaneous wound model by culture in allogenic species-specific serum and administration in fibrin constructs", Stem Cells, 2006, vol. 24, pp. 2232-2243.
Griffiths, S. et al., "Human platelet lysate stimulates high-passage and senescent human multipotent mesenchymal stromal cell growth and rejuvenation in vitro", Cytotherapy, 2013, vol. 15, pp. 1469-1483.
Komoda, H. et al., "Reduction of N-glycolylneuraminic acid xenoantigen on human adipose tissue-derived stromal cells/mesenchymal stem cells leads to safer and more useful cell sources for various stem cell therapies", Tissue Engineering: Part A; 2010, vol. 16, No. 4, pp. 1143-1155.

* cited by examiner

*Primary Examiner* — Louise W Humphrey
*Assistant Examiner* — Stephen A Perkins
(74) *Attorney, Agent, or Firm* — Troutman Sanders, LLP

(57) ABSTRACT

The present invention is directed towards methods for producing cell and tissue compositions suitable for therapeutic applications to a mammal in need of a therapeutic cell or tissue treatment. In particular, the invention is directed towards a method of culturing cells for use in therapy, which method comprises (i) culturing a sample of cells in a first cell culture medium and (ii) prior to harvesting cells for use in therapy culturing the cells in a second cell culture medium.

6 Claims, 5 Drawing Sheets

CELL CULTURE METHOD

CROSS-REFERENCE TO RELATED APPLICATIONS

This application is a United States national stage entry of an International Application serial no. PCT/AU2014/001031 filed Nov. 3, 2014 which claims priority to Australian provisional patent application No. 2013904257 entitled "Cell culture method" and filed Nov. 4, 2013. The contents of these applications are incorporated herein by reference in their entirety as if set forth verbatim.

FIELD

The present invention relates to novel and improved methods and compositions for cell and tissue therapy. The invention relates to methods for producing cell and tissue compositions suitable for therapeutic applications to a mammal in need of a therapeutic cell or tissue treatment.

BACKGROUND

Cell therapy is an increasingly important treatment for several types of disorders, injuries, malignancies and diseases. Cell therapy involves the infusion, application or transplant of cells to a patient, whereby the infused, applied or transplanted cells are either derived from a donor other than the patient (allogeneic) or from the patient themselves (autologous). Mesenchymal stromal cells (MSC) are one cell type that has shown promise for therapeutic use.

Despite their promise, the clinical results obtained to date with MSC have been generally poor. The major reason for these poor clinical outcomes appears to be due the way the MSC have been produced. For example, most MSC are cultured in fetal calf serum which is then removed by simply washing the cells post-harvest. However, this simple washing may not remove bovine proteins attached to the cell surface or those located within the cells which may later be incorporated into the external cell surface. These cells, on implantation, will then appear foreign to patients with antibodies to bovine proteins present in their blood (incidence approximately 40-50% Australian population), be recognised by the patient's immune system and be destroyed before delivering their therapeutic benefit.

Thus, there is a continuing need for methods of producing cells for cell therapy.

SUMMARY

The inventors have discovered that cells can be produced in such a way that the issues with the current production methods are improved or resolved, which has led to enhanced clinical outcomes.

Accordingly, in a first aspect, the present invention provides a method of culturing cells for use in therapy comprising the steps of:
(i) culturing a sample of cells in a first cell culture medium comprising a first serum, first serum substitute and/or first serum fraction for sufficient time to enable the cells to achieve a desired level of expansion; and
(ii) prior to harvesting cells for use in therapy said first cell culture medium is replaced with a second cell culture medium comprising a second serum, a second serum substitute and/or second serum fraction and the cells are cultured for a further period of time.

In a second aspect, the present invention provides a method of culturing human mesenchymal stromal cells for use in cell therapy comprising the steps of:
(i) culturing mesenchymal stromal cells in a first cell culture medium comprising DMEM supplemented with heat inactivated fetal calf serum (HIFCS) until said cells reach about 70-85% confluence; and
(ii) about 24 hours before harvesting cells for use in therapy said first cell culture medium is removed and replaced with a second cell culture medium comprising DMEM phenol red-free and about 2% human serum albumin and the cells are then cultured for a further about 24 hours.

In a third aspect, the present invention provides a method of culturing human mesenchymal stromal cells for use in cell therapy comprising the steps of:
(i) culturing between $1.0 \times 10^3$ cells per $cm^2$ of culture vessel and $1.0 \times 10^{10}$ cells per $cm^2$ of culture vessel of mesenchymal stromal cells in a first cell culture medium comprising DMEM supplemented with heat inactivated fetal calf serum (HIFCS) until said cells reach about 70-85% confluence; and
(ii) about 24 hours before harvesting cells for use in therapy said first cell culture medium is removed and replaced with a second cell culture medium comprising DMEM phenol red-free and about 2% human serum albumin and the cells are then cultured for said about 24 hours.

In a fourth aspect, the present invention provides a method for preparing cells for allogeneic cell therapy in a patient comprising the steps of:
(i) providing a sample of cells from a healthy donor;
(ii) culturing said sample of cells in a first cell culture medium comprising a first serum, first serum substitute and/or first serum fraction for sufficient time to enable the cells to achieve a desired level of expansion; and
(ii) prior to harvesting cells for use in therapy said first cell culture medium is replaced with a second cell culture medium comprising a second serum, a second serum substitute and/or second serum fraction and the cells are cultured for a further period of time; and
(iv) harvesting said cells.

It will be appreciated by those skilled in the art that step (i) of the method requires the sample of cells to metabolise, expand or proliferate in cell number until the culture vessel holding the cells reaches a level of confluence to be harvested. Thus, the culture conditions including media should be sufficient to allow optimal expansion of the cultured cells.

In some embodiments, the preferred serum in the first cell culture medium is fetal calf serum (FCS) or heat inactivated fetal calf serum (HIFCS). However, it will be appreciated that other sources of nutrients, hormones and protein can be used instead of FCS including serum albumin which is a major component of FCS. Also other serum substitutes such as platelet lysate and commercial products such as those sold under the trademarks ULTROSER® G serum substitute (Pall Corporation, NY, USA); HIT® serum substitute which contains human serum albumin, insulin and transferrin in ISCOVE'S MDM® (Stemcell Technologies, BC, Canada); Serum Substitute Supplement™ (SSS™) consists of 6% total protein: containing approximately 84% human serum albumin, 16% alpha and beta globulins and <1% gamma globulins (Irvine Scientific, CA, USA); and QUINNS ADVANTAGE® serum protein substitute (CooperSurgical Inc, CT, USA). All of these serum substitutes provide the right osmotic potential, growth factors and nutrients/proteins to enable the sample of cells to adhere to the culture vessel and expand in cell number.

In some embodiments, the first cell culture medium comprises a serum fraction such as serum albumin.

The second medium comprises a second serum or second serum fraction which has the same species origin as the cells being cultured. For example, if human cells are being cultured then the second medium will comprise human serum, human serum substitute or human serum albumin. If equine cells are being cultured then the second medium will comprise horse serum, horse serum substitute or horse serum albumin. Similarly, if canine cells are cultured then the second medium will comprise canine serum etc.

It will be appreciated by those skilled in the art that the sample of cells can comprise any cell that can be used in cell therapy including allogeneic and autologous hepatic cells, allogeneic and autologous hemopoietic cells, allogeneic and autologous fibroblast cells, allogeneic and autologous adipose cells, allogeneic and autologous mesenchymal cells, allogeneic and autologous cardiac cells, allogeneic and autologous endothelial cells, allogeneic and autologous epithelial cells, allogeneic and autologous neuronal cells, allogeneic and autologous glial cells, allogeneic and autologous endocrine cells, or progenitor cells thereof.

Preferably, the cells of the present invention are mesenchymal progenitor cells in particular mesenchymal stromal cells (MSC).

It is to be understood that the methods and compositions of the present invention may be used for cell therapy in any mammalian animal. Accordingly, the sample of cells may be isolated from a human, a cameline, an equine, a canine and a feline or any other commercially or economically valuable mammalian animal.

It will be appreciated by those skilled in the art that the first medium, while containing a first serum, a first serum substitute and/or first serum fraction as discussed supra, will also comprise a base medium. There are many base medium known in the art, but preferred base medium can be selected from the group consisting of those sold under the trademarks DMEM® (high or low glucose), EAGLE'S BASAL MEDIUM® (MEM®), HAM'S F10 MEDIUM® (F10®), HAM'S F-12 MEDIUM® (F12®), ISCOVE'S MODIFIED DULBECCO'S MEDIUM®, M-199, MESENCHYMAL STEM CELL GROWTH MEDIUM® (MSCGM®), LIEBOVITZ'S L-15 MEDIUM®, MCDB®, DMEM/F12, RPMI 1640, advanced DMEM® (GIBCO®), DMEM/MCDB201 (SIGMA®), and CELL-GRO FREE® or a combination thereof. Preferably, the first base medium is a medium sold under the trademark DMEM®.

Preferably, the first base medium is supplemented with heat inactivated fetal calf serum (HIFCS).

The cell or tissue culture methods are standard methods well known in the art. These include temperature range e.g. about 37° C., $CO_2$ concentration e.g. 10% $CO_2$ and the like. Also the amount of cells in the sample of cells will be approximately those used in standard cell culture procedures. For example, in some embodiments the cell number in the cell sample will be between $1.0 \times 10^3$ cells per cm$^2$ of culture vessel and $1.0 \times 10^{10}$ cells per cm$^2$ of culture vessel. This number of cells will equate to approximately $12 \times 10^6$ per 80 cm$^2$ tissue culture flask or $28 \times 10^6$ per 175 cm$^2$ tissue culture flask.

In some embodiments, the sample of cells in step (i) of the preferred method are cultured until the cells are approximately 85% confluent. It will be appreciated by persons skilled in the art that this might include regular changes of the first base medium to keep the medium fresh. At this stage the cells are either processed further, for example, step (ii) of the inventive method or passaged.

If the cells are to be harvested for use in cell therapy the first culture medium is removed and replaced with a second culture medium. Step (ii) is performed at least 12 hours before the cells are harvested for use in cell therapy. Preferably, step (ii) is performed at least 18 hours before the cells are harvested for use in cell therapy. Even more preferably, step (ii) is performed at least 24 hours before the cells are harvested for use in cell therapy.

It will also be appreciated that the cells cannot be allowed to remain in contact with the second culture medium for longer than about 48 hours as the cells will start to become senescent. Accordingly, in some embodiments, step (ii) is performed between about 24 hours and about 36 hours before the cells are harvested for use in cell therapy.

In some aspects the cells in step (ii) will be cultured in the presence of the second culture medium for 12, 13, 14, 15, 16, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 and 48 hours.

The second medium in step (ii) typically comprises a base medium selected from the group consisting of those sold under the trademarks DMEM® (high or low glucose), EAGLE'S BASAL MEDIUM® (MEM®), HAM'S F10 MEDIUM® (F10®), HAM'S F-12 MEDIUM® (F12®), ISCOVE'S MODIFIED DULBECCO'S MEDIUM®, M-199, MESENCHYMAL STEM CELL GROWTH MEDIUM® (MSCGM®), LIEBOVITZ'S L-15 MEDIUM®, MCDB®, DMEM/F12, RPMI 1640, advanced DMEM® (GIBCO®), DMEM/MCDB201 (SIGMA®), and CELL-GRO FREE® or a combination thereof. Preferably, the second base medium is a medium sold under the trademark DMEM® phenol red-free.

In some embodiments, the second base medium is supplemented with human serum or human serum albumin. While the amount of human serum or human serum albumin used in the second medium is not restricted i.e. any amount of serum may be used, in some embodiments the amount of human serum or human serum albumin is about 2%.

It will be appreciated by those skilled in the art that the methods of the present invention can be used on cells, in an allogeneic or autologous setting. In the allogeneic setting the donor and recipient may or may not be matched.

In a fifth aspect, the present invention provides a composition for use in cell therapy comprising cells produced by the method according to any one aspects 1 to 4.

In some embodiments, the cells have a phenotype comprising >90% CD73, >90% CD90, >90% CD105 expression and <5% CD34, <5% CD45, <5% CD14 expression. In further embodiments, the cells have a phenotype comprising CD54, CD61, CD89, CD140A and CD201 expression. The expression of CD54, CD61, CD89, CD140A and CD201 is increased relatively to human mesenchymal stromal cells that have been cultured in methods other than the methods of the invention as described herein.

It will be appreciated by those skilled in the art that the cells can be provided in a range of delivery devices. For example, in some embodiments the cells are suspended in a syringe, while in others the cells are suspended in a collapsible container. Preferably, the cells are suspended in a media suitable for therapeutic administration to a patient.

In a sixth aspect, the present invention provides a method of cell therapy comprising:
(i) providing a sample of cells from a healthy donor;
(ii) culturing said sample of cells in a first cell culture medium comprising a first serum, first serum substitute and/or first serum fraction for sufficient time to enable the cells to achieve a desired level of expansion; and
(ii) prior to harvesting cells for use in therapy said first cell culture medium is replaced with a second cell culture medium comprising a second serum, a second serum substitute and/or second serum fraction and the cells are cultured for a further period of time;
(iv) harvesting said cells; and
(v) implanting or administering said cells to a patient in need thereof.

It will be appreciated by those skilled in the art that once the expanded cells of the present invention have been produced they may be stored for later use. Further, the expanded cells may be provided in the form of a kit, comprising a sample of cells and relevant reagents, such as culture media, and instructions for culturing and use.

Accordingly, in a seventh aspect, the present disclosure provides a kit comprising an expanded population of cells produced by the method of the first aspect.

In some embodiments, the cells of the present invention may be incubated in a monolayer or a 3-dimensional culture. In order to obtain 3-dimensional cultures it will be appreciated by those skilled in the art that suitable scaffolds can be used. Suitable scaffolds for include one sold under the trademark VITROGEN®, a collagen-containing solution which gels to form a cell-populated matrix, and the connective-tissue scaffolds of Hwang (US patent application no. 20040267362), Kladaki et al (US patent application no. 20050177249) and Binette et al (US patent application no. 20040078077).

The cells of the present invention may also be applied to any of a wide variety of contacting surfaces of medical devices. Contacting surfaces include, but are not limited to, surfaces that are intended to contact blood, cells or other bodily fluids or tissues of an animal, including specifically a human. Suitable contacting surfaces include one or more surfaces of medical devices that are intended to contact blood or other tissues. The medical devices include aneurysm coils, artificial blood vessels, artificial hearts, artificial valves, artificial kidneys, artificial tendons and ligaments, blood bags, blood oxygenators, bone and cardiovascular replacements, bone prostheses, bone waxes, cardiovascular grafts, cartilage replacement devices, catheters, microbeads, nerve-growth guides, ophthalmic implants, orthopaedic implants, prosthetics, shunts, stents, wound coverings, wound healing devices and other medical devices known in the art.

The contacting surface may include a mesh, coil, wire, inflatable balloon, or any other structure which is capable of being implanted at a target location, including intravascular locations, intralumenal locations, locations within solid tissue, and the like. The implantable device can be intended for permanent or temporary implantation. Such devices may be delivered by or incorporated into intravascular and other medical catheters.

Accordingly, in eighth aspect, the present invention provides a medical device comprising an expanded population of cells produced by the method of the first aspect.

In a ninth aspect, the present invention provides a use of human mesenchymal stromal cells in the manufacture of a medicament useful in cell therapy, wherein said human mesenchymal stromal cells are produced by:

(i) culturing said mesenchymal stromal cells in a first cell culture medium comprising DMEM supplemented with heat inactivated fetal calf serum (HIFCS) until said cells reach about 70-85% confluence;
(ii) about 24 hours before harvesting cells for use in therapy said first cell culture medium is removed and replaced with a second cell culture medium comprising DMEM phenol red-free and about 2% human serum albumin and the cells are then cultured for a further about 24 hours;
(iii) harvesting said mesenchymal stromal cells in a pharmaceutically acceptable medium, diluent or carrier, suitable for therapeutic administration to a patient.

In a tenth aspect, the present invention provides a cell culture medium for in vitro culturing of human mesenchymal stromal cells for use in human therapy, the culture medium comprising human serum or human serum albumin in an amount sufficient to allow an increase in the expression of one or more adhesion markers on the human mesenchymal stromal cell surface relative to human mesenchymal stromal cells that are not cultured in the presence of human serum or human serum albumin.

In some embodiments, the cell surface markers that have increased expression are selected from the group consisting of CD54, CD61, CD89, CD140A and CD201.

In an eleventh aspect the present invention provides an in vitro cultured human mesenchymal stromal cell, which cell expresses on its cell surface one or more markers selected from the group consisting of CD54, CD61, CD89, CD140A and CD201, wherein said markers are preferentially expressed than naturally occurring mesenchymal stromal cells.

BRIEF DESCRIPTION OF THE FIGURES

FIG. 2 *b*: Actuarial survival by response, chronic cases and time since first MSC infusion.

DESCRIPTION OF THE PREFERRED EMBODIMENTS OF THE INVENTION

Figure 1:
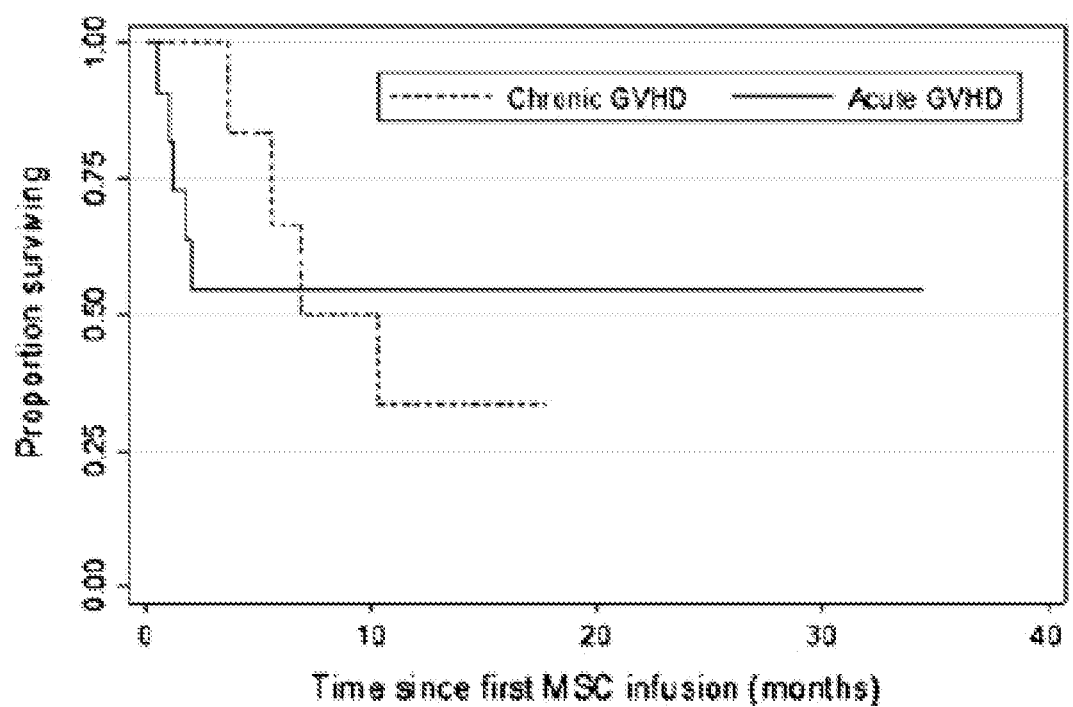
FIG. 1: Actuarial survival, time since first MSC infusion.

Before describing the present invention in detail, it is to be understood that this invention is not limited to particularly exemplified methods of production, which may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional immunological techniques, cell biology and tissue culture techniques and medical techniques within the skill of the art. Such techniques are well known to the skilled worker, and are explained fully in the literature. See, e.g., Coligan, Dunn, Ploegh, Speicher and Wingfield "Current Protocols in Protein Science" (1999) Volume I and II (John Wiley & Sons Inc.); and Bailey, J. E. and Ollis, D. F., Biochemical Engineering Fundamentals, McGraw-Hill Book Company, NY, 1986; Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

It must be noted that as used herein and in the appended claims, the singular forms "a," "an," and "the" include plural reference unless the context clearly dictates otherwise. Thus, for example, a reference to "a cell" includes a plurality of such cells, and a reference to "an animal" is a reference to one or more animals, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In one of the broadest aspects, the present invention relates to a method of culturing cells for use in therapy.

The terms "culturing," "culture," and "cultured" are used interchangeably herein and generally refers to standard cell and tissue culture techniques used to grow cells in vitro. Standard techniques include, but are not limited to, isolation techniques for obtaining cells, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. For a review of clonal selection and cell separation techniques, see Freshney, Culture of Animal Cells. A Manual of Basic Techniques, 2 d Ed., A. R. Liss, Inc., New York, 1987, Ch. 11 and 12, pp. 137-168.

The phrase "a sample of cells" or "cells of the invention" refers to the isolation or supply of cells for culturing and then therapy. As the methods of the invention may be used on any mammalian animal cell the sample of cells may be isolated from any mammalian animal species including but not limited to, a human, a cameline, an equine, a canine, or a feline or any other commercially or economically valuable mammalian animal.

The term "isolated" indicates that the cell or cell population to which it refers is not within its natural environment. The cell or cell population has been substantially separated from surrounding tissue. In some embodiments, the cell or cell population is substantially separated from surrounding tissue if the sample contains at least about 75%, in some embodiments at least about 85%, in some embodiments at least about 90%, and in some embodiments at least about 95% cells. In other words, the sample of cells is substantially separated from the surrounding tissue and the sample contains less than about 25%, in some embodiments less than about 15%, and in some embodiments less than about 5% of materials other than the cells. Such percentage values refer to percentage by cell number. The term encompasses cells which have been removed from the organism from which they originated, and exist in culture. The term also encompasses cells which have been removed from the organism from which they originated, and subsequently re-inserted into an organism. The organism which contains the re-inserted cells may be the same organism from which the cells were removed, or it may be a different organism.

It will be appreciated by those skilled in the art that the sample of cells can comprise any cell that can be used in cell therapy including allogeneic and autologous hepatic cells, allogeneic and autologous hemopoietic cells, allogeneic and autologous fibroblast cells, allogeneic and autologous adipose cells, allogeneic and autologous mesenchymal cells, allogeneic and autologous cardiac cells, allogeneic and autologous endothelial cells, allogeneic and autologous epithelial cells, allogeneic and autologous neuronal cells, allogeneic and autologous glial cells, allogeneic and autologous endocrine cells, or progenitor cells thereof.

In some embodiments, the cells of the present invention are mesenchymal progenitor cells in particular mesenchymal stromal cells (MSC). In some embodiments, the MSC's are not produced from embryonic material, but comprise adult mesenchymal stromal cells.

The cell population of the invention may also be characterised in that the cells do not express a particular selection of markers at a detectable level. As defined herein, these markers are said be to be negative markers.

In some embodiments, the cell population of the invention is considered not to express a marker if at least about 70% of the cells of the isolated cell population should not show detectable expression of the marker. In other embodiments, at least about 80%, at least about 90% or at least about 95% or at least about 97% or at least about 98% or at least about 99% or 100% of the cells of the cell population should not show any detectable expression of the marker. Again, lack of detectable expression may be proven through the use of an RT-PCR experiment or using FACS.

The negative markers described above are considered not to be expressed by a cell population of the invention, if expression cannot be reasonably detected at a level of 30 cycles of PCR, which corresponds to an expression level in the cell of less than about 100 copies per cell.

In one embodiment, the cell population is further characterised in that the cells do not express one, two or all three of the markers CD14, CD34 and CD45 at a detectable level. As described above, it is possible for these markers not to be expressed despite a small amount of residual expression persisting.

The cell population of the invention may also be characterised in that the cells do express a particular selection of markers at a detectable level. As defined herein, these markers are said be to be positive markers.

In some embodiments, the cell population of the invention is considered to express a marker if at least about 70% of the cells of the isolated cell population shows detectable expression of the marker. In other embodiments, at least about 80%, at least about 90% or at least about 95% or at least about 97% or at least about 98% or at least about 99% or 100% of the cells of the cell population show detectable expression of the marker. Detectable expression may be proven through the use of an RT-PCR experiment or using FACS.

The positive markers described above are considered to be expressed by a cell population of the invention, if expression is reasonably detected at a level of 30 cycles of PCR, which corresponds to an expression level in the cell of more than about 100 copies per cell.

In one embodiment, the cell population is further characterised in that the cells express one, two or all three of the markers CD73, CD90 and CD105 at a detectable level.

The term CD73 includes CD73 and any orthologs thereof, including but not limited to NTSE, 5'-nucleotidase, ecto, RP11-321N4.1, ESNT, NT, NTS, NTE, eN, eNT, 5' nucleotidase (CD73), 5' nucleotidase, OTTHUMP00000040565, Purine 5-Prime-Nucleotidase, and ecto-5'-nucleotidase.

The term CD90 includes CD90 and any orthologs thereof, including but not limited to Thy-1, 5E10.

The term CD105 includes CD105 and any orthologs thereof, including but not limited to ENG, endoglin, RP11-228B15.2, END, FLJ41744, HHT1, ORW, and ORW1.

In some embodiments, the cells have a phenotype comprising >90% CD73, >90% CD90, >90% CD105 expression and <5% CD34, <5% CD45, <5% CD14 expression.

In some embodiments, the preferred sample of cells is bone marrow mononuclear cells isolated from bone marrow aspirate. Bone marrow aspirate may be collected into a heparinised syringe from the harvest needle. If the time from collection to processing will be longer than 2 hours, the marrow is preferably stored chilled (2-8° C.) and processing commenced within 24 hours.

In some embodiments, the bone marrow mononuclear cells are separated by density gradient centrifugation and washed in PBS before being resuspended in a first cell culture medium and plated.

The number of cells that are plated will depend upon the cell type and the type of culture vessel. However, the cell number will typically be between $1.0 \times 10^3$ cells per $cm^2$ of culture vessel and $1.0 \times 10^{10}$ cells per $cm^2$ of culture vessel. In some embodiments, the number of cells equates to approximately $12 \times 10^6$ per 80 $cm^2$ tissue culture flask or $28 \times 10^6$ per 175 $cm^2$ tissue culture flask.

The phrase "first cell culture medium" is used herein to refer to standard culture medium that allows the sample of cells to metabolise, expand or proliferate in cell number until the culture vessel holding the cells reaches a level of confluence to be harvested.

The terms "culture medium" or "medium" or "media" are recognized in the art, and refers generally to any substance or preparation used for the cultivation of living cells. The term "medium", as used in reference to a cell culture, includes the components of the environment surrounding the cells.

The "first cell culture medium" will typically include a first base medium (e.g. commercially available medium) such as those sold under the trademarks DMEM® (high or low glucose), EAGLE'S BASAL MEDIUM® (MEM®), HAM'S F10 MEDIUM® (F10®), HAM'S F-12 MEDIUM® (F12®), ISCOVE'S MODIFIED DULBECCO'S MEDIUM®, M-199, MESENCHYMAL STEM CELL GROWTH MEDIUM® (MSCGM®), LIEBOVITZ'S L-15 MEDIUM®, MCDB®, DMEM/F12, RPMI 1640, advanced DMEM® (GIBCO®), DMEM/MCDB201 (SIGMA®), and CELL-GRO FREE® or a combination thereof. In some embodiments, the first base medium is a medium sold under the trademark DMEM®.

The "first cell culture medium" will also typically include a first serum, a first serum substitute, a first serum fraction or combination thereof. The term "first serum" includes commercially available serum sources such as fetal calf serum (FCS) or heat inactivated fetal calf serum (HIFCS). Preferably, the first base medium is supplemented with heat inactivated fetal calf serum (HIFCS).

The term "first serum substitutes" include platelet lysate and commercial products such as those sold under the trademarks ULTROSER® G serum substitute (Pall Corporation, NY, USA); HIT® serum substitute which contains human serum albumin, insulin and transferrin in ISCOVE'S MDM® (Stemcell Technologies, BC, Canada); SERUM SUBSTITUTE SUPPLEMENT® (SSS®) consists of 6% total protein: containing approximately 84% human serum albumin, 16% alpha and beta globulins and <1% gamma globulins (Irvine Scientific, CA, USA) and QUINNS ADVANTAGE® serum protein substitute (CooperSurgical Inc, CT, USA). All of these serum substitutes provide the right osmotic potential, growth factors and nutrients/proteins to enable the sample of cells to adhere to the culture vessel and expand in cell number.

The term "first serum fraction" includes serum components such as serum albumin.

Once the first sample of cells is plated the cells are incubated under standard cell culture conditions for sufficient time to expand and reach a required level of confluency. One typical set of cell culture conditions is about 37° C., about 5% $CO_2$ and about 70% humidity.

The phrase "sufficient time" refers to the length of time for the cells to achieve a "desired level of expansion". It will be appreciated by those skilled in the art that the time required to reach a desired level of expansion will depend on certain factors such as the cell type, the initial plating cell density, the type of first cell culture medium and the number of cells required for the end use therapy. However, in some embodiments the cells are incubated for between 18 and 72 h, before adherent cells are washed with PBS and media replaced for continued culture.

The phrase "desired level of expansion" typically involves the step of growing the cells until the cells have reached 70 to 90% confluency with media changes every 3-4 days. In some embodiments, the cells can be grown in cell factories such as one sold under the trademark CELL-STACK® factories (Corning, USA). Cells are seeded into these factories at typical cell densities of about 5,000 cells/$cm^2$. As described infra, the number of cells used in therapy is between about $1 \times 10^6$ cells/kg body weight to about $15 \times 10^6$/kg body weight. Thus, for an 80 kg person approximately $80 \times 10^6$ cells to $1200 \times 10^6$ cells in total will be required. Thus, in some embodiments, the phrase "desired level of expansion" means culturing the cells until a desired volume of cells has been produced such as $80 \times 10^6$ cells to $1200 \times 10^6$ cells.

Once the cells have reached the desired level of expansion the cells can be prepared for harvesting. The phrase "prior to harvesting cells" as used herein refers to the replacement of the "first cell culture medium" with a "second cell culture medium". The time period to which the term "prior" refers to is typically at least 12 hours before the cells are harvested for use in cell therapy. Preferably, this step is performed at least 18 hours before the cells are harvested for use in cell therapy. Even more preferably, step (ii) is performed at least 24 hours before the cells are harvested for use in cell therapy. Thus, typically the first cell culture medium is removed and replaced with a second cell culture medium and the cells on then incubated at about 37° C. in a humidified incubator containing 5% $CO_2$ for about 24 h. It will also be appreciated that the cells cannot be allowed to remain in contact with the second cell culture medium for longer than about 48 hours as the cells will start to become senescent.

It will be appreciated that the phrase "cells are cultured for a further period of time" refers to the same period of time as encompassed by the term "prior".

The phrase "second cell culture medium" as used herein refers to a tissue culture medium which comprises a base medium selected from the group consisting of those sold under the trademarks DMEM® (high or low glucose), EAGLE'S BASAL MEDIUM® (MEM®), HAM'S F10 MEDIUM® (F10®), HAM'S F-12 MEDIUM® (F12®), ISCOVE'S MODIFIED DULBECCO'S MEDIUM®, M-199, MESENCHYMAL STEM CELL GROWTH MEDIUM® (MSCGM®), LIEBOVITZ'S L-15 MEDIUM®, MCDB®, DMEM/F12, RPMI 1640, advanced DMEM® (GIBCO®), DMEM/MCDB201 (SIGMA®), and CELL-GRO FREE® or a combination thereof. Preferably, the second base medium is a medium sold under the trademark DMEM® phenol red-free.

The "second cell culture medium" will also comprise "a second serum," "a second serum substitute," "a second serum fraction" or combination thereof. However, it is critical that the second serum and/or second serum fraction has the same species origin as the cells being cultured. For example, if human cells are being cultured then the second medium will comprise human serum, human serum substitute or human serum albumin. If equine cells are being cultured then the second medium will comprise horse serum, horse serum substitute or horse serum albumin. Similarly, if canine cells are cultured then the second medium will comprise canine serum etc.

In some embodiments, the second base medium is supplemented with human serum or human serum albumin for use in culturing human cells. While the amount of human serum or human serum albumin used in the second medium is not restricted i.e. any amount of serum may be used, in some embodiments the amount of human serum or human serum albumin is about 2%.

Without wishing to be bound by any theory or hypothesis, the inventors believe that culturing cells for therapy in serum that is not "matched" to the species of origin eg human serum for human cells, canine serum for canine cells, etc, the cultured cells produced express surface markers that are recognized by the patient's immune system as "foreign" which leads to tissue rejection issues and ultimately failure in treatment. However, culturing cells in species matched serum eg human serum for too long is (i) costly and (ii) produced sufficient cells for therapy too slowly. Accordingly, it is preferential to culture cells for therapy in "standard" tissue culture medium such as one sold under the trademark DMEM® and fetal calf serum and then remove the "first cell culture medium" to be replaced with the "second cell culture medium" of the present invention, which allows the removal of the erroneous cell surface markers.

With the above in mind, it should be noted that following the step of culturing the cells of the invention in the second cell culture medium, the cells have an "increase in the expression of one or more adhesion markers." The term "increase in the expression" refers to an increase in the amount of detectable mRNA encoding an adhesion marker protein or the detection of adhesion marker protein per se. The increase is relative to the level of detection of mRNA and/or protein for these adhesion markers on cells that have not been cultured in the presence of the second cell culture medium or more specifically have been cultured in the presence of fetal calf serum supplemented medium such as the medium used in the first cell culture medium. Techniques for measuring the increase of mRNA and/or protein are well known in the field and are referred to supra.

The terms "harvest," and "harvesting" are used herein to refer to the process of collecting the expanded cells for use in therapy. Standard techniques for removing cells from cell culture flasks and factories may be used. For example, it is well know that trypsin may be used to remove adherent cells from plastic cell culture flasks. One preferred method involves the removal of the second cell culture medium from the cell factory by aspiration; rinsing of the cells with PBS; adding trypsin eg one sold under the trademark TRYPLE SELECT® (Life Technologies Inc, CA, USA); incubation at 37° C. until all cells have detached, usually within 30 min, but less than 1 hour. The cells are then isolated in media. The cells are then centrifuged for 5 min at 450 g (1500 rpm) and resuspended in the appropriate suspension medium and counted.

The cells in the appropriate suspension medium at the appropriate cell number for therapy constitutes a cell therapy composition as defined herein.

The "appropriate suspension medium" will depend upon the therapy, route of administration, cell type and the like, but typically the suspension medium is an isotonic solution suitable for intravenous use. Preferably the isotonic solution further comprises about 2% HSA.

The "appropriate cell number" is again dependent of the therapy being undertaken, route of administration, cell type and the like.

It will be appreciated by those skilled in the art that once the expanded cells of the present invention have been produced, they may be stored for later use. The techniques for preparing the cells of the invention for cryopreservation will depend upon the end use for the cells. If, for example, the cryopreservation is for subculture, then the cells can be harvested as described supra in appropriate media e.g. one sold under the trademark DMEM® supplemented with 10% HIFBS and 5 µg/mL gentamicin, and an equal volume of a cryopreservation solution of 80% cell culture medium e.g. one sold under the trademark DMEM® supplemented with 10% HIFBS and 5 µg/mL gentamicin plus 20% DMSO (dimethyl sulphoxide). Alternatively, if, for example, the cryopreservation is for future patient administration, then the cells can be harvested in an isotonic solution which preferably contains 2% HSA, then centrifuged and the supernatant removed. The cells can then be resuspended in an isotonic solution and an equal volume of a cryopreservation solution comprising, for example, 40% isotonic solution, 40% HSA (20% solution) and 20% DMSO. The cells are initially chilled to 2-8° C. then controlled rate frozen to −160° C.

The procedure for thawing the cells will again depend upon the end use. For example, thawing cells that are to be cultured typically involves rapid thawing in a water bath containing sterile saline, pre-heated to 36-40° C., until just thawed. The cells are then washed in PBS, centrifuged at 450 g (1500 rpm) for 5 min and resuspended in media to obtain required cell concentration.

For patient use, the cryopreserved cells are thawed rapidly in a water bath containing sterile saline, pre-heated to 36-40° C., until just thawed. The cells are then diluted with an equal amount of an isotonic solution and infused within 5 hours of thawing.

As described supra, the methods of the present invention can be used on allogeneic or autologous cells. Thus, in some embodiments the "donor" is a matched donor, while in other embodiments the "donor" is not matched. For example, the donor might have less than or equal to a 50% tissue match to the patient, but in other circumstances there will be no match at all i.e. allogeneic donor.

In some embodiments, the cells of the present invention are mixed with one or more pharmaceutically acceptable carriers. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject cells from one organ, or portion of the body, to another organ, or portion of the body. Each carrier must be "acceptable" in the sense of being compatible with the other ingredients of the material being administered and not injurious to the patient.

The pharmaceutically acceptable carrier may comprise a cell culture medium which supports the cells' viability. The medium will generally be serum-free in order to avoid provoking an immune response in the recipient. The carrier will generally be buffered and/or pyrogen-free.

Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. In many embodiments, the solution is stable under the conditions of manufacture and storage and preserved against the contaminating action of microorganisms such as bacteria and fungi through the use of, for example, parabens, chlorobutanol, phenol, ascorbic acid, thimerosal. This list is provided by way of illustration only, and is not intended to be limiting. Solutions that are cell compositions of the invention can be prepared by incorporating cells as described herein in a pharmaceutically acceptable carrier or diluent and, as required, other ingredients enumerated above, which have been sterilized by filtration.

Some examples of materials and solutions which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations. This list is provided by way of illustration only, and is not intended to be limiting.

Once the cells have been prepared as described herein then they can be used in therapy to treat patients. Generally, the terms "treating," "treatment" and the like are used herein to mean affecting an individual or animal, their tissue or cells to obtain a desired pharmacological and/or physiological effect. The effect is especially therapeutic in terms of a partial or complete cure of a condition and/or disorder. "Treating" as used herein covers any treatment of a condition and/or disorder in a vertebrate, a mammal, particularly a human, and includes: (a) inhibiting the condition and/or disorder, i.e., arresting its development; or (b) relieving or ameliorating the symptoms of the condition and/or disorder.

The terms "condition" and/or "disorder" are used herein interchangeably and refers to abnormal conditions affecting animals, including humans, which can be treated using the cells of the present invention.

As described throughout the specification the cells of the invention are particularly suitable for cellular therapies, including the induction of tissue repair/regeneration in vivo. Therefore, the invention provides a method of treating a patient, wherein the method comprises administering cells of the invention to the patient in an appropriate amount.

Generally the cells of the invention or progeny thereof are introduced into the body of the patient by infusion, injection or implantation. The cells may be infused or directly injected or implanted into the tissue in which they are intended to act. A syringe containing cells of the invention and a pharmaceutically acceptable carrier is included within the scope of the invention. A catheter attached to a syringe containing cells of the invention and a pharmaceutically acceptable carrier is included within the scope of the invention.

As discussed above, the cells of the invention can be used in the regeneration of tissue. In order to achieve this function, cells may be injected or implanted directly into the damaged tissue, where they exert an action, may multiply and eventually may differentiate into the required cell type, in accordance with their location in the body. Tissues that are susceptible to treatment include all damaged tissues, particularly including those which may have been damaged by disease, injury, trauma, an autoimmune reaction, or by a viral or bacterial infection.

In one embodiment the cells of the invention or progeny thereof, either in solution, in microspheres or in microparticles of a variety of compositions, will be administered into the artery irrigating the tissue or the part of the damaged organ in need of regeneration. Generally such administration will be performed using a catheter. The catheter may be one of the large varieties of balloon catheters used for angioplasty and/or cell delivery or a catheter designed for the specific purpose of delivering the cells to a particular local of the body. Although the cells exhibit a strong tropism for certain tissues (e.g. myocardium) for certain indications, it may be desirable to note that most of the cells administered to the patient do not go through the capillary network and into the systemic circulation. For certain uses, the cells may be encapsulated into microspheres made of a number of different biodegradable compounds, and with a diameter of about 15 µm. This method may allow intravascularly administered cells to remain at the site of damage, and not to go through the capillary network and into the systemic circulation in the first passage. The retention at the arterial side of the capillary network may also facilitate their translocation into the extravascular space.

In another embodiment, the cells may be retrograde injected into the vascular tree, either through a vein to deliver them to the whole body or locally into the particular vein that drains into the tissue or body part to which the cells are directed. For this embodiment many of the preparations described above may be used.

An alternative embodiment for the treatment of the myocardium is a transcatheter injection transendocardically, with or without electric mapping with a system such as the Noga system or any similar injection system.

In another embodiment, the cells of the invention or progeny thereof may be implanted into the damaged tissue adhered to a biocompatible implant. Within this embodiment, the cells may be adhered to the biocompatible implant in vitro, prior to implantation into the patient. As will be clear to a person skilled in the art, any one of a number of adherents may be used to adhere the cells to the implant, prior to implantation. By way of example only, such adherents may include fibrin, one or more members of the integrin family, one or more members of the cadherin family, one or more members of the selectin family, one or more cell adhesion molecules (CAMs), one or more of the immunoglobulin family and one or more artificial adherents. This list is provided by way of illustration only, and is not intended to be limiting. It will be clear to a person skilled in the art, that any combination of one or more adherents may be used.

In another embodiment, the cells of the invention or progeny thereof may be embedded in a matrix, prior to implantation of the matrix into the patient. Generally, the matrix will be implanted into the damaged tissue of the patient. Examples of matrices include collagen based matrices, fibrin based matrices, laminin based matrices, fibronectin based matrices and artificial matrices. This list is provided by way of illustration only, and is not intended to be limiting.

In a further embodiment, the cells of the invention or progeny thereof may be implanted or injected into the patient together with a matrix forming component. This may allow the cells to form a matrix following injection or implantation, ensuring that the cells remain at the appropriate location within the patient. Examples of matrix forming components include fibrin glue liquid alkyl, cyanoacrylate monomers, plasticizers, polysaccharides such as dextran, ethylene oxide-containing oligomers, block co-polymers such as poloxamer and one sold under the trademark PLURONICS® (BASF), non-ionic surfactants such as those sold under the trademarks TWEEN® (Croda Americas) and TRITON 8® (DOW), and artificial matrix forming components. This list is provided by way of illustration only, and is not intended to be limiting. It will be clear to a person skilled in the art, that any combination of one or more matrix forming components may be used.

In a further embodiment, the cells of the invention or progeny thereof may be contained within a microsphere. Within this embodiment, the cells may be encapsulated within the centre of the microsphere. Also within this embodiment, the cells may be embedded into the matrix material of the microsphere. The matrix material may include any suitable biodegradable polymer, including but not limited to alginates, Poly ethylene glycol (PLGA), and polyurethanes. This list is provided by way of example only, and is not intended to be limiting.

In a further embodiment, the cells of the invention or progeny thereof may be adhered to a medical device intended for implantation. Examples of such medical devices include stents, pins, stitches, splits, pacemakers, prosthetic joints, artificial skin, and rods. This list is provided by way of illustration only, and is not intended to be limiting. It will be clear to a person skilled in the art, that the cells may be adhered to the medical device by a variety of methods. For example, the cells may be adhered to the medical device using fibrin, one or more members of the integrin family, one or more members of the cadherin family, one or more members of the selectin family, one or more cell adhesion molecules (CAMs), one or more of the immunoglobulin family and one or more artificial adherents. This list is provided by way of illustration only, and is not intended to be limiting. It will be clear to a person skilled in the art, that any combination of one or more adherents may be used.

In another embodiment the cells of the invention can be administered into the peripheral circulation and through their tropism for the tissue of origin it can be expected that the cells will home to the organ/tissue to be treated.

As described above, for use in medicine, the cells will be delivered to the patient in a therapeutically effective amount. The number of cells to be delivered in vivo or ex vivo may be based on a number of parameters, including: the body weight of the patient, the severity of tissue damage, and the number of cells surviving within the subject. A typical number of cells may be around $10^6$ to $10^9$ cells. It may be necessary to repeat infusion, injection or implantation of the cells for up to several years to achieve the necessary cumulative total mass and/or to replace cells which are dying. Generally, the total number of cells delivered to the patient in a single treatment regiment will be greater than about $1 \times 10^6$. However, the total number of cells delivered may be higher than $1 \times 10^{10}$. The patient or recipient will usually receive at least one dose of cells. Preferably the patient or recipient will receive, 1, 2, 3, 4, 5, 6, 7, 8, 9, 10, 11, 12, 13, 14, 15, 16, 17, 18, 19, 20 or more doses.

The cells may be given as a single dose, multiple doses over defined time period, or up to and including routine chronic maintenance dosing. The doses of cells will typically be spaced apart. For example, the doses might be 1 to 2 days apart or weekly or monthly. In some embodiments, the doses are weekly for 4 weeks.

Further within the invention, the isolated cells of the invention are used in the manufacture of a medicament for use in tissue regeneration or cell therapy, including but not limited to Crohn's disease, graft versus host disease, regeneration of the liver, certain areas of the nervous system, such as those associated with Parkinson's disease, and the pancreas. Such regeneration may allow the treatment of Parkinson's disease, type II diabetes, chronic skin ulcers, and autoimmune disorders. The cells of the present invention can also be used to treat high grade primary glioma or lower grade recurrent brain tumours such as glioma, ependymoma, medulloblastoma or teratogenic tumours, severe peripheral arterial disease, tendon repair, multiple myeloma, leukaemia, cornea damage, scleroderma, multiple sclerosis, systemic lupus erythematosus (SLE), vasculitis, Behcet's disease, osteoarthritis, cartilage repair and rheumatoid arthritis. This list is provided by way of illustration, and is not intended to be limiting.

The cells of the present invention may also be applied to any of a wide variety of contacting surfaces of medical devices. Contacting surfaces include, but are not limited to, surfaces that are intended to contact blood, cells or other bodily fluids or tissues of an animal, including specifically a human. Suitable contacting surfaces include one or more surfaces of medical devices that are intended to contact blood or other tissues. The medical devices include aneurysm coils, artificial blood vessels, artificial hearts, artificial valves, artificial kidneys, artificial tendons and ligaments, blood bags, blood oxygenators, bone and cardiovascular replacements, bone prostheses, bone waxes, cardiovascular grafts, cartilage replacement devices, catheters, contact lenses, containers for cell and tissue culture and regeneration, embolization particles, filtration systems, grafts, guide channels, in-dwelling catheters, laboratory instruments, microbeads, nerve-growth guides, ophthalmic implants, orthopaedic implants, pacemaker leads, probes, prosthetics, shunts, stents, supports for peptides, surgical instruments, sutures, syringes, urinary tract replacements, wound coverings, wound dressings, wound healing devices and other medical devices known in the art.

Other examples of medical devices that would benefit from the application of the present invention will be readily apparent to those skilled in the art of surgical and medical procedures and are therefore contemplated by the instant invention. The contacting surface may include a mesh, coil, wire, inflatable balloon, or any other structure which is capable of being implanted at a target location, including intravascular locations, intralumenal locations, locations within solid tissue, and the like. The implantable device can be intended for permanent or temporary implantation. Such devices may be delivered by or incorporated into intravascular and other medical catheters.

Further, the expanded cells may be provided in the form of a kit, system or procedure pack, containing individually packaged therapeutic goods, and may include combinations of medicines, medical devices and biologicals.

By "comprising" is meant including, but not limited to, whatever follows the word comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The invention will now be further described by way of reference only to the following non-limiting examples. It should be understood, however, that the examples following are illustrative only, and should not be taken in any way as a restriction on the generality of the invention described above.

Example 1 Manufacturing Process for Mesenchymal Stromal Cells (MSC) of the Invention Bone marrow mononuclear cells were separated by density gradient centrifugation and washed cells were resuspended in media sold under the trademark DMEM® (INVITROGEN®, Australia) supplemented with 10% fetal bovine serum (FBS) (SABC Biosciences, Australia) (a representative example of the "first cell culture medium" of the present invention as described herein) and plated at a density of 160,000 cells per cm².

Cultures were maintained at 37° C. in a humidified incubator containing 5% $CO_2$ for 18-72 h, before adherent cells were washed with PBS (DKSH, Australia) and fresh first media replaced for continued culture. Cells were grown to 80-90% confluency with media changes every 3-4 days and then passaged using media sold under the trademark TRYPLE-SELECT® (INVITROGEN®, Australia) and reseeded at a density of 5,000 cells/cm² in media sold under the trademark CELLSTACK® factories (Corning, USA). After expansion, usually at passage 2 or 3, the media comprising FBS was removed and replaced with media sold under the trademark DMEM® phenol red-free (INVITROGEN®, Australia) supplemented with 2% human serum albumin (HSA) (ARCBS) (a representative example of a "second cell culture medium" of the present invention as described herein). The MSC produced by this method were then incubated at 37° C. in a humidified incubator containing 5% $CO_2$ for 24 h. The cells were then harvested and administered or cryopreserved in 10% dimethyl sulfoxide (WAK-Chemie, Germany), 50% media sold under the trademark PLASMA-LYTE® (Baxter Health Care, Sydney Australia), 20% sodium chloride solution and 20% human serum albumin and stored at −196° C. Cell expansion was limited to passage 5 with cytogenetic analysis carried out at final passage. Cells were prepared to allow for doses of 1-10×10⁶ cells/kg patient body weight.

MSC were deemed available for clinical use provided they met the following release criteria: micro-contamination testing of the final product by aerobic and anaerobic culture (media sold under the trademarks BACTEC PLUS AEROBE/F® and BACTEC PLUS ANAEROBE/F®, BD) was negative, cell viability by trypan blue exclusion was greater than 70% and there was expression of characteristic MSC immunophenotype (expression of CD73, CD90 and CD105 and lack of CD45, CD34 and CD14 expression) as analysed by flow cytometry on an FACS Canto machine, using FACS Diva software.

Example 2 Cell Surface Expression

Cell surface phenotyping was performed using the Becton Dickinson's screening panel sold under the trademark BD LYOPLATE® screening panels, which are the first comprehensive systems available for the efficient profiling of hundreds of murine and human cell surface markers by flow cytometry or bioimaging. The panels were used by following the manufacturers' instructions. Cells of the invention were produced using the methodology described in Example 1 and as a comparator other samples of MSC were cultured for the same period of time as in Example 1, but without the final culturing step in the presence of human serum albumin. The expression of 242 markers was then screened via high-throughput flow cytometry and we found that a number of cell surface markers were differentially expressed. For example, CD54, CD61, CD89, CD140A and CD201 had increased expression in cells grown in media containing human serum albumin as compared to media containing fetal calf serum. These markers are mainly adhesion markers.

Example 3 Use of Mesenchymal Stromal Cells of the Invention in Therapy for Steroid-Refractory Acute and Chronic Graft Versus Host Disease Significant advances in understanding the biology, and prevention and treatment of graft versus host disease (GVHD) have been made over the last two decades, leading to the introduction of second-line agents such as the anti-tumour necrosis factor (TNF) and anti-CD25 biologics. However, the prognosis for steroid-refractory acute GVHD remains poor with around 20% long-term survival (Deeg, (2007), *Blood,* 109(10): 4119-26). The incidence of acute GVHD grades II-IV is approximately 50% after allogeneic haematopoietic stem cell transplantation (HSCT). Standard treatment is with high-dose corticosteroids, usually methylprednisolone 2 mg/kg IV or oral equivalent, which induces a durable complete response in around 30-40% of patients (MacMillan et al., (2002), *Biol Blood Marrow Transplant;*

8(7): 387-94). With steroid-refractory chronic GVHD (CGVHD), long-term survival is diminished and disabling morbidity is common.

We investigated whether the MSC's produced by the method of Example 1 were capable of treating steroid-refractory acute and chronic graft versus host disease.

Between March 2007 and July 2010, patients with acute and CGVHD who signed informed consent were eligible to receive MSC in a single institution phase 1 safety trial. The study was approved by the Ethics Committee, Royal Perth Hospital and granted a Clinical Trials Notification (CTN) by the Australian regulatory authority, the Therapeutics Goods Administration (TGA). The trial was registered with the Australian and New Zealand Clinical Trials Registry (AN-ZCTR12610000068066).

All allogeneic transplant patients received prophylaxis against AGVHD with a calcineurin inhibitor and 4 doses of methotrexate. Pre-transplant conditioning was myeloablative in 14 patients and non-myeloablative in 7 patients. The haematopoietic stem cell source was mobilised peripheral blood cells in all patients.

Patients with AGVHD aged 18 years or above were eligible for the study if AGVHD grades II-IV had failed to respond or progressed after 7 days' treatment with intravenous methylprednisolone 2 mg/kg or oral prednisolone 2.5 mg/kg. AGVHD was assessed by the consensus grading (Przepiorka et al. (1995), Bone Marrow Transplant; 15(6): 825-8). All patients continued with steroid therapy and a calcineurin inhibitor and all started concomitant second-line therapy with etanercept 25 mg subcutaneously twice weekly. Etanercept is a soluble dimeric TNFα receptor 2, which competes for TNF binding and renders TNF inactive. A biopsy-confirmed diagnosis of AGVHD was required for trial entry. Patients with a poor performance status, who were not expected to survive 7 days, were excluded.

Chronic GVHD patients had extensive disease despite prednisolone 2.5 mg/kg and a calcineurin inhibitor and usually received mycophenolate, but were not required to do so as part of the protocol. They were classified according to the NIH Consensus Criteria with the major target organ(s) having a score of 2 or more (Filipovich et al., (2005), Biol. Blood Marrow Transplant; 11(12): 945-56).

The primary end point of the trial was safety, and secondary end points were best response and overall survival. For AGVHD, complete response was loss of all symptoms and signs of AGVHD, and partial response was at least an improvement of one grade or more. For CGVHD, complete response was as for AGVHD and partial response was an improvement in the NIH consensus score of at least one (Filipovich et al., (2005), supra).

Donors were required to be less than 60 years of age, not have medical comorbidities and to sign informed consent. They also had to have negative infectious disease markers as required by the TGA for blood and tissue donation.

Nineteen patients were enrolled between January 2007 and June 2010, 12 with AGVHD and 7 with CGVHD. Patient characteristics and response are shown in Table 1 for AGVHD and Table 2 for CGVHD.

TABLE 1

Characteristics And Response Of AGVHD Subjects

| Patient, Gender, Age | Donor | Conditioning | Primary Diagnosis | Time Since Allograft At First Infusion (Months) | Source of MSC | Signs of AGVHD | AGVHD Stage (Grade) | No. of Infusions | Response By Organ (And Stage Where PR) | Outcome |
|---|---|---|---|---|---|---|---|---|---|---|
| UPN 1, M, 21 | MUD | Cy/TBI (M) | C ALL, Relapse | 5 | Non-HLA matched sibling | Hepatic Skin Mucositis | 1 3 4 (III) | 19 | Hepatic CR Skin CR Mucositis CR | CR, off immunosuppression |
| UPN 4, F, 23 | MUD | Bu/Mel (M) | MDS | 6 | 3rd Party | Skin Oral mucositis | 3 4 (III) | 5 | Skin CR Mucositis CR | CR Died of recurrent sepsis |
| UPN 6, M, 53 | MUD | Flu/TBI (M) | CLL | 1 | 3rd Party | Skin Gut | 4 3 (IV) | 8 | Skin CR Gut PR(1) | Died of viral and fungal sepsis |
| UPN 8, F, 29 | MUD | Flu/Mel (M) | AML | 1 | 3rd Party | Skin | 3 (III) | 2 | Skin CR | CR |
| UPN 9, M, 56 | MUD | Flu/Mel (NM) | NHL | 5 | 3rd Party | Skin Gut | 2 2 (II) | 2 | Skin CR Gut CR | CR |
| UPN 11, M, 58 | MUD | Flu/Mel (NM) | AML | 10 | 3rd Party | Skin Gut | 3 3 (III) | 2 | Skin PR(1) Gut PR(1) | Died of gut sepsis |
| UPN 12, M, 61 | MUD | Bu/Flu (NM) | RAEB2T | 4 | 3rd Party | Skin Gut | 3 3 (IIII) | 2 | Skin CR Gut PR(1) | Died of gut sepsis |
| UPN 13, F, 47 | Sib | Bu/Mel (M) | Secondary AML | 1 | 3rd Party | Skin Gut | 3 3 (III) | 2 | Skin CR Gut CR | CR |
| UPN 15, M, 25 | MUD | Bu/Mel (M) | CML BC | 4 | 3rd Party | Hepatic Skin Gut | 1 4 3 (IV) | 2 | Hepatic CR Skin CR | CR |
| UPN 16, F, 47 | Sib | Cy/TBI (M) | CLL | 6 | Matched sibling | Gut Skin | 2 4 (IV) | 2 | Gut CR Skin CR | CR |
| UPN 17, M, 50 | MUD | Bu/Mel (M) | PRV to MF | 4 | 3rd Party | Gut Liver | 3 2 (III) | 2 | Gut PR(1) Liver NR | Died Haemorrhagic stroke |

TABLE 1-continued

Characteristics And Response Of AGVHD Subjects

| Patient, Gender, Age | Donor | Conditioning | Primary Diagnosis | Time Since Allograft At First Infusion (Months) | Source of MSC | Signs of AGVHD | AGVHD Stage (Grade) | No. of Infusions | Response By Organ (And Stage Where PR) | Outcome |
|---|---|---|---|---|---|---|---|---|---|---|
| UPN 18, M, 52 | MUD | Flu/Mel (NM) | NHL | 1 | 3rd Party | Skin Mucositis | 4 4 (IV) | 2 | Skin NR Mucositis NR | NR Died of sepsis |

MUD matched unrelated donor,
Sib matched sibling,
Cy cyclophosphamide,
TBI total body irradiation,
Bu busulfan,
Mel melphalan,
Flu fludarabine,
M myeloablative,
NM non-myeloablative,
CALL common acute lymphoblastic leukaemia,
MDS myelodysplasia,
CLL chronic lymphocytic leukaemia,
AML acute myeloid leukaemia,
NHL non-Hodgkin's lymphoma,
RAEBT refractory anaemia with excess of blasts in transformation,
CML BC chronic myeloid leukaemia in blast crisis,
PRV polycythemia rubra vera,
MF myelofibrosis,
CR complete response,
PR partial

TABLE 2

Characteristics And Response Of CGVHD Subjects

| Patient, Gender, Age | Donor | Conditioning | Primary Diagnosis | Time Since Allograft At First Infusion (Months) | Source of MSC | Signs of CGVHD & Score | No. of Infusions | Response By Organ (Score achieved where PR) | Outcome |
|---|---|---|---|---|---|---|---|---|---|
| UPN 2, M, 51 | Sib | Bu/Mel (M) | AML | 63 | Sib | O.B 3 KCS 2 | 8 | O.B NR KCS PR(1) | Recurrent chest infections and death |
| UPN 3, M, 50 | Sib | Cy/TBI (M) | Ph + ALL | 85 | Sib | O.B 3 KCS 2 | 8 | O.B NR KCS PR(1) | Respiratory failure death |
| UPN 5, F, 36 | MUD | Bu/Mel (M) | AML | 89 | Sib | Skin 2 | 7 | Skin CR | CR |
| UPN 7, M, 31 | MUD | TBI/Mel (M) | AML | 18 | 3rd Party | Oral Mucositis 3 | 8 | CR | CR |
| UPN 10, M, 34 | MUD | Bu/Mel (M) | ALL | 14 | 3rd Party | Oral Mucositis 3 | 3 | Mucositis PR(2) | Died of progressive leukaemia |
| UPN 14, F, 53 | MUD | Flu/Mel (NM) | CML BC | 27 | Haploid Son | O.B 2 Skin 2 | 2 | O.B NR Skin PR(1) | Died of chest infection, respiratory failure |
| UPN 19, M, 48 | Sib | Bu/Mel (M)) | AML | 20 | 3rd Party | Hepatic 3 | 11 | Liver NR | NR Died of liver failure |

MUD matched unrelated donor,
Sib matched sibling donor,
Haploid haploidentical,
Bu busulfan,
Mel melphalan,
Cy cyclophosphamide,
TBI total body irradiation,
AML acute myeloid leukaemia,
Ph + ALL Philadelphia positive acute lymphoblastic leukaemia,
CML BC chronic myeloid leukaemia in blast crisis,
OB obliterative bronchiolitis,
KCS keratoconjunctivitis sicca,
CR complete response,
PR partial All patients had a haematologic malignancy. Patients who received a matched unrelated donor transplant represented 10 of the 12 with AGVHD and 2 of 7 with CGVHD.

Initially, patients received 8 infusions of MSC twice weekly for 4 weeks intravenously, either as inpatients in the case of AGVHD or in a day centre for CGVHD patients, and were monitored for infusion-related reactions. Subsequently, after the publication of a randomised trial comparing two doses of MSC for AGVHD (Kebriaei et al., 2009), *Biol Blood Marrow Transplant;* 15(7): 804-11), a trial amendment was made to two infusions at weekly intervals and nine patients received infusions on this basis. Patients who achieved but did not maintain a complete response were eligible for retreatment with two infusions at weekly intervals. Complete response was loss of all signs of GVHD, partial response was improvement by one grade, stable disease was no change in the symptoms or signs of GVHD, and progression was a deterioration of one grade or more.

Safety was assessed by observation of the patient for 4 h after each infusion, monitoring vital signs for infusional reactions. Patients were also asked on subsequent visits for infusion about symptoms experienced during the interval after the previous infusion and monitored for adverse events at regular ongoing follow-up.

Given that this was a phase I study, we restricted the statistical methods to descriptive methods which indicate the overall experience of the patients stratified into acute and chronic categories. Survival was described as time from first MSC infusion. The Kaplan-Meier method was used to estimate survival times separately for acute and chronic cases. The non-parametric log-rank test was used to examine differences in survival between groups and to examine trends in survival patterns for ordered groups.

MSC for this study were derived from a bone marrow aspirate from a total of 16 haploidentical family members or HLA-mismatched, related or unrelated donors. MSC were manufactured according to the methods described in Example 1.

A total of 109 infusions were administered to the 19 patients with a median of 2 infusions per patient. Two patients required further infusions for relapse of AGVHD with one patient having one episode of reinfusion and the second receiving 7 infusions over 3 years. Six patients with CGVHD received 2 infusions in one treatment episode and one patient with CGVHD had more than one treatment episode, receiving a total of 11 infusions. Apart from mild abnormalities in taste due to the cryoprotectant dimethyl sulfoxide noticed in several patients, the infusions were tolerated well with no acute infusion-related toxicities and no subsequent toxicities attributable to MSC infusions noted.

The response by organ involved and the overall response are shown in Table 1 for AGVHD and Table 2 for CGVHD. The response rate overall for AGVHD was complete in 7, partial in 4, and no response in one patient. All the patients who did not have a complete response died: 5 of opportunistic infection and one from a haemorrhagic stroke. Of the seven patients who achieved a complete response, 6 are alive and one died of bacterial sepsis.

Figure 2A:
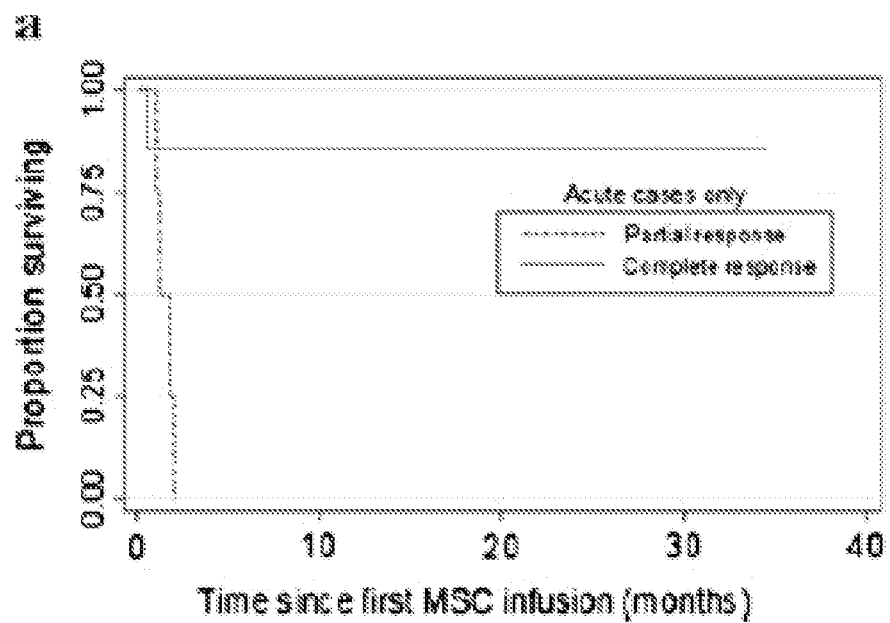
FIG. 2 *a*: Actuarial survival by response, acute cases and time since first MSC infusion.
Figure 2B:
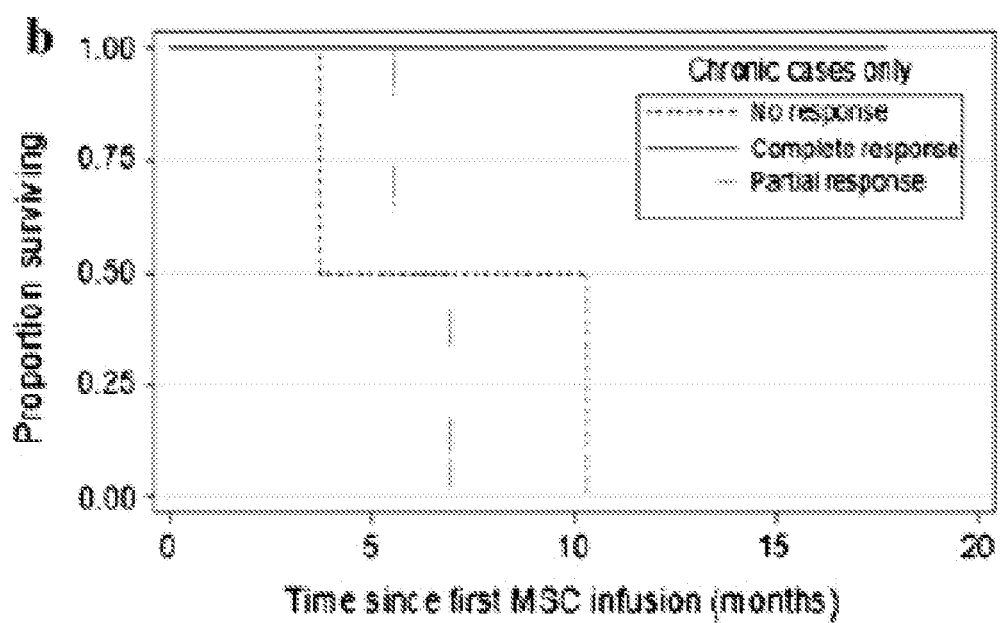

Two patients with CGVHD achieved a complete response, while 2 achieved partial responses and 3 had no response. There were 5 deaths in this group, 3 from progressive obliterative bronchiolitis associated with chest infections, one from liver failure due to CGVHD and one from relapsed acute lymphoblastic leukaemia. The actuarial survival for both groups is shown in FIG. 1, with 3-year survival of 55% for the acute group and median survival for CGVHD of 8 months. In AGVHD, complete response was important for survival. The logrank test showed that response was a statistically significant predictor of survival for acute GVHD patients ($\chi 2=11.3$, $p=0.0008$) (FIG. 2*a*), but not for chronic cases ($\chi 2=2.79$, $p=0.100$) (FIG. 2*b*).

This study reports the safe infusion of 109 doses of donor-derived MSC cultured and stored under GMP conditions. The lack of early and late infusion-related toxicity reflects both the quality of the manufactured product, as well as the innate immune-privileged status of MSC. In summary, we identified no safety issues, early or later in our group of 19 patients.

Example 4 Use of Allogeneic Mesenchymal Stromal Cells of the Invention in Therapy for Luminal Crohn's Disease Refractory to Biologic Therapy Despite the advent of biologic therapy for Crohn's disease (CD), about one-quarter of patients still need major abdominal surgery within five years after diagnosis1. In order to avoid surgery, cellular therapy by bone marrow or peripheral blood stem cell transplantation, either allogeneic or autologous, has been successfully used in small numbers of patients, but requires prior myeloablative therapy or hematopoietic stem cell mobilisation (Hommes et al. (2011), *J Crohns Colitis;* 5: 543-549).

By contrast, MSC are multipotent adult stem cells which are considered to lack immunogenicity and hence escape immune recognition; they have low level HLA class I expression, lack HLA class II antigen, and do not express co-stimulatory molecules. Accordingly, in allogeneic administration, donor to recipient matching is neither required, nor chemotherapeutic marrow conditioning (Le Blanc et al. (2003), *Exp Hematol;* 31: 890-896).

As we demonstrated supra in Example 2, the MSC of our invention successfully treated steroid refractory GVHD. We hypothesized that our MCSs could also be used to treat luminal Crohn's Disease that was refractory to other biologic therapy.

Our phase 2, open-label, multi-centre study included 16 patients (21-55 y old; 6 male) with infliximab- or adalimumab-refractory, endoscopically confirmed, active luminal CD (CD activity index [CDAI]>250). Subjects were given intravenous infusions of allogeneic MSC as prepared in Example 1 ($2 \times 10^6$ cells/kg body weight) weekly for 4 weeks. The primary endpoint was clinical response (decrease in CDAI>100 points) 42 days after the first MSC administration; secondary endpoints were clinical remission (CDAI<150), endoscopic improvement (a CD endoscopic index of severity [CDEIS] value<3 or a decrease by >5), quality of life, level of C-reactive protein, and safety.

The following inclusion criteria applied: colonic or small bowel CD (based on endoscopy and histology); CDAI>250; endoscopically active disease; disease refractory to induction with infliximab or adalimumab, or loss of response to both, or side effects to either or both of these drugs precluding further use. Failure to induce remission was defined as failure of clinical remission four weeks after a minimum three doses of infliximab (5 mg/kg) at 0, 2 and 6 weeks; or three doses of adalimumab (160 mg, week 0; 80 mg, week 2; 40 mg, week 4). The following exclusion criteria applied: chronic stricturing disease without inflammation; co-existent bacterial entero-colitis or cytomegalovirus (CMV) infection; prior malignancy; pregnancy or unwilling for birth control during therapy; breastfeeding; stoma (CDAI not measurable); or active sepsis, including perianal sepsis or perforating disease. The following applied regarding concomitant drug therapy: last biologic (infliximab or adalimumab) four or more weeks prior; and between t=−14 days and day 42, stable doses of corticosteroid (within 10 mg prednisolone variation), immunomodulator (azathioprine, 6-mercaptopurine, methotrexate) or antidiarrhoeal.

Figure 3:
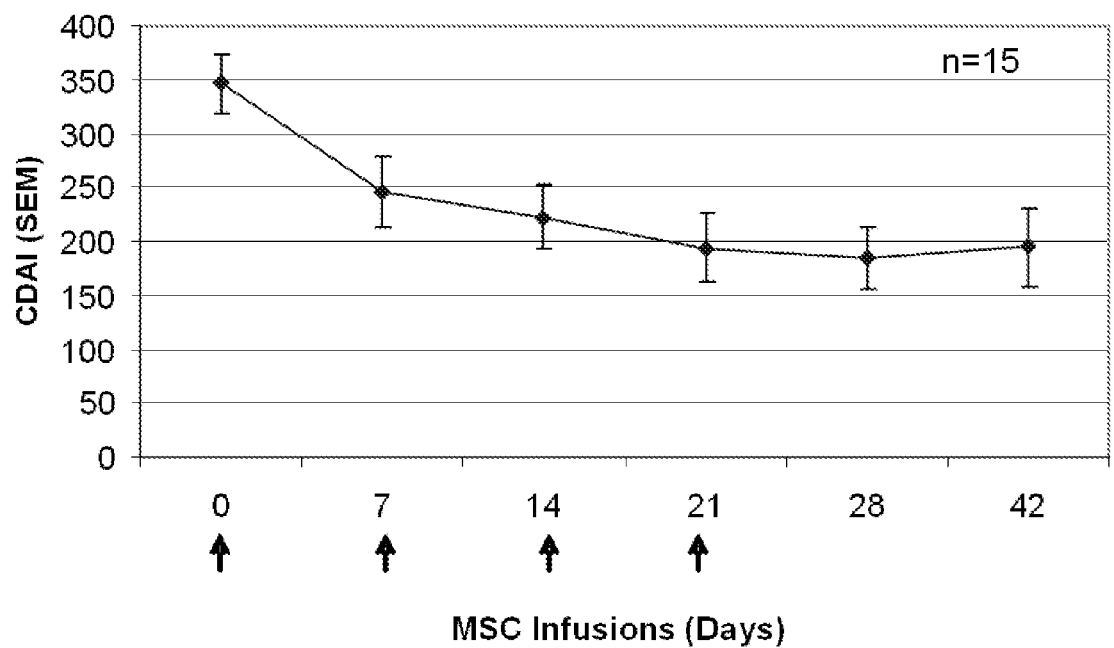
FIG. 3: Mean Crohn's Disease Activity Index (CDAI) over the study period.
Figure 4:
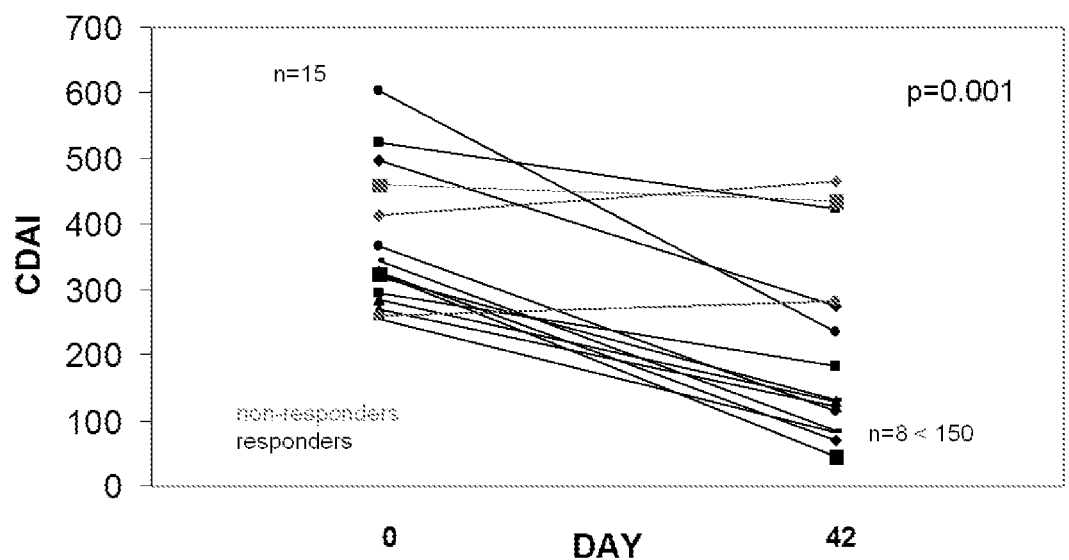
FIG. 4: Crohn's Disease Activity Index (CDAI) Pre & Post MSC Treatment.

Among the 15 patients who completed the study, the mean CDAI score was reduced from 370 (median, 327; range, 256-603) to 203 (median, 129) at day 42 (P<0.0001). Mean CDAI scores decreased after each MSC infusion (370 before administration, 269 on day 7, 240 on day 14, 209 on day 21, 182 on day 28, and 203 on day 42). FIG. 3 shows the mean Crohn's Disease Activity Index (CDAI) over the study period. Twelve patients had a clinical response (80%; 95% confidence interval, 72%-88%; mean reduction in CDAI, 211; range 102-367), 8 had clinical remission (53%; range, 43%-64%; mean CDAI at day 42, 94; range 44-130). FIG. 4 shows the Crohn's Disease Activity Index (CDAI) pre and post MSC treatment. Seven patients had endoscopic improvement (47%), for whom mean CDEIS scores decreased from 21.5 (range, 3.3-33) to 11.0 (range, 0.3-18.5). One patient had a serious adverse event (2 dysplasia-associated lesions), but this was probably not caused by MSC.

Table 3 shows the demographics of the study, while Tables 4 and 5 shows the outcome evaluations.

| Patient Number | Age | Gender | Distribution Of Disease | Entry CDAI | Prior Biologic/ Immunomodulator Therapy | Prior Surgery | Anti-TNF Prior To MSC (Weeks Prior To Last Dose) *Primary Failure | Concomitant Drug Therapy During Study# | Total MSC Dose |
|---|---|---|---|---|---|---|---|---|---|
| 1 | 25 | F | Colitis | 414 | Infliximab Adalimumab Azathioprine | Perianal abscess drainage/ insertion of seton | Adalimumab 4 weeks | | $9.4 \times 10^6$/kg |
| 2 | 55 | M | Colitis | 524 | Infliximab Adalimumab Azathioprine | Nil | Adalimumab 4 weeks | Azathioprine Prednisolone 10 mg | $8.2 \times 10^6$/kg |
| 3 | 31 | F | Colitis | 269 | Infliximab Adalimumab Azathioprine | Subtotal colectomy | Adalimumab 8 weeks | Prednisolone 12.5-15 mg# Prednisolone enema | $9.8 \times 10^6$/kg |
| 4 | 32 | F | Colitis | 319 | Infliximab Adalimumab Azathioprine | Nil | Adalimumab 4 weeks* | Azathioprine | $9.8 \times 10^6$/kg |
| 5 | 23 | F | Colitis | 325 | Infliximab Adalimumab Azathioprine | Nil | Adalimumab 4 weeks | Prednisolone 20 mg | $7.1 \times 10^6$/kg |
| 6 | 39 | F | Colitis | 603 | Infliximab 6MP | Perianal abscess drainage/ insertion of seton | Adalimumab 6 months | Mycophenolate Mofetil Ciprofloxacin | $8.0 \times 10^6$/kg |
| 7 | 21 | M | Colitis | 366 | Infliximab Adalimumab Azathioprine | Nil | Adalimumab 4 weeks* | 6MP Prednisolone 25-15 mg# | $8.6 \times 10^6$/kg |
| 8 | 27 | F | Colitis | 344 | Infliximab Adalimumab Azathioprine | Perianal abscess drainage/ insertion of seton | Adalimumab 3 months | Azathioprine Prednisolone 15 mg | $8.3 \times 10^6$/kg |
| 9 | 52 | M | Colitis | 256 | Infliximab Adalimumab Azathioprine | Perianal abscess drainage | Adalimumab 4 weeks | 6MP | $8.0 \times 10^6$/kg |
| 10 | 39 | F | Colitis + Perianal | 498 | Infliximab Adalimumab Azathioprine Methotrexate | Nil | Infliximab 12 months | Azathioprine Prednisolone 35 mg | $9.3 \times 10^6$/kg |
| 11 | 31 | M | Colitis + Perianal | 295 | Infliximab Adalimumab 6MP | Nil | Infliximab 4 months | 6MP Prednisolone 35 mg | $10.1 \times 10^6$/kg |
| 12 | 41 | M | Ileocolitis | 285 | Infliximab Adalimumab Azathioprine | Ileocolonic resection | Adalimumab 4 weeks | Azathioprine | $8.6 \times 10^6$/kg |
| 13 | 46 | F | Ileocolitis | 327 | Infliximab Adalimumab Azathioprine | Nil | Adalimumab 10 weeks | Prednisolone 20-15 mg# | $9.0 \times 10^6$/kg |
| 14 | 35 | M | Colitis + Perianal | 397 | Infliximab Adalimumab Azathioprine Methotrexate | Perianal abscess drainage/ insertion of seton and temporary ileostomy | Adalimumab 6 weeks | Methotrexate Prednisolone 10 mg | $9.4 \times 10^6$/kg |
| 15 | 23 | M | Colitis | 259 | Infliximab Adalimumab Azathioprine | Nil | Adalimumab 4 weeks | Prednisolone 10 mg | $9.7 \times 10^6$/kg |
| 16 | 52 | F | Ileal | 460 | Adalimumab Azathioprine 6MP | Ileocolonic/ileal resections x 3 | Adalimumab 4 weeks* | Loperamide | $8.8 \times 10^6$/kg |

*primary failure of a single biologic; all other patients failed both biologies
where variation of prednisolone dose is given, initial dose figure represents study entry dose, and last figure the study endpoint dose

TABLE 4

CDAI and endoscopic outcome data

| Patient Number | CDAI Entry | CDAI d 7 | CDAI d 14 | CDAI d 21 | CDAI d 28 | CDAI d 42 | Clinical Response | Clinical Remission | CDEIS Entry | CDEIS d 42 | Endoscopic Improvement |
|---|---|---|---|---|---|---|---|---|---|---|---|
| 1 | 414 | 315 | 330 | 329 | 324 | 466 | N | N | 9.75 | 17.5 | N |
| 2 | 524 | 504 | 392 | 320 | 338 | 422 | Y | N | 19 | 18.5 | N |
| 3 | 269 | 160 | 143 | — | 147 | 122 | Y | Y | 19.5 | 19.5 | N |
| 4 | 319 | 149 | 186 | 201 | 193 | 130 | Y | Y | 23 | 18.5 | Y |
| 5 | 325 | 76 | 180 | 108 | 88 | 44 | Y | Y | 17 | 9.5 | Y |
| 6 | 603 | 362 | 437 | 169 | 160 | 236 | Y | N | 26 | 25.3 | N |
| 7 | 366 | 189 | 113 | 68 | 107 | 114 | Y | Y | 27.5 | 17.5 | Y |
| 8 | 344 | 382 | 223 | 256 | 177 | 85 | Y | Y | 3.3 | 0.3 | Y |
| 9 | 256 | 182 | 159 | 80 | 46 | 81 | Y | Y | 19 | 9.75 | Y |
| 10 | 498 | 338 | 256 | 281 | 135 | 275 | Y | N | 32.5 | 31 | N |
| 11 | 295 | 245 | 234 | 222 | 175 | 180 | Y | N | 28 | 8.6 | Y |
| 12 | 285 | 210 | 227 | 169 | 169 | 128 | Y | Y | 33 | 13 | Y |
| 13 | 327 | 97 | 8 | 20 | 0 | 50 | Y | Y | 6.1 | 10.2 | N |
| 14 | 397 | 389 | 291 | 202 | — | — | — | — | 18 | — | — |
| 15 | 259 | 277 | 276 | 244 | 236 | 282 | N | N | 31.5 | 32 | N |
| 16 | 460 | 454 | 390 | 472 | 436 | 436 | N | N | 9.1 | 6.25 | N |

TABLE 5

Quality of life and C-reactive protein outcome data

| Patient number | IBDQ entry | IBDQ d 42 | AQoL entry | AQoL d 42 | CRP entry | CRP d 42 |
|---|---|---|---|---|---|---|
| 1 | 136 | 115 | 87 | 95 | 23 | 45 |
| 2 | 111 | 148 | 73 | 67 | 4.1 | 3.1 |
| 3 | 151 | 138 | 73 | 67 | 48 | not measured |
| 4 | 104 | 160 | 85 | 64 | 9.5 | 5.5 |
| 5 | 107 | 184 | 98 | 58 | 6.6 | 4.4 |
| 6 | 85 | 143 | 79 | 79 | 21 | 16 |
| 7 | 136 | 207 | 67 | 41 | 13 | 2.9 |
| 8 | 99 | 161 | 90 | 72 | 2.9 | 5 |
| 9 | 150 | 115 | 58 | 43 | 20 | 1.9 |
| 10 | 103 | 148 | 73 | 61 | 36.9 | 36 |
| 11 | 129 | 162 | 85 | 67 | 3.1 | 1.4 |
| 12 | 125 | 176 | 100 | 77 | 13 | 18 |
| 13 | 91 | not available | 80 | not available | 6 | not available |
| 14 | 88 | not measured | 117 | not measured | 38 | not measured |
| 15 | 142 | 152 | 76 | 81 | 30 | 13 |
| 16 | 93 | 94 | 96 | 104 | 2.3 | 6.1 |

Our data suggests efficacy of intravenous allogeneic MSC in luminal CD. In 15 patients with moderate to severe active disease, refractory to anti-TNF therapy, four infusions of $2 \times 10^6$ cell/kg at weekly intervals led to clinical response in 12 (80%), clinical remission in eight (53%), and endoscopic improvement in seven (47%). Quality of life improved, in parallel with improvement in CDAI (Irvine et al., (1994), *Gastroenterol;* 106: 287-296). Our data are the first to demonstrate effectiveness for luminal disease in a convincing way.

What is claimed is:

1. A method of culturing human mesenchymal stromal cells for use in allogeneic therapy comprising the steps of:
   (i) providing a sample of said cells from a donor to a first culture medium;
   (ii) culturing said cells in the first cell culture medium comprising fetal calf serum, for at least 18 hours until said cells are at least 70% confluent;
   (iii) replacing said first cell culture medium with a second cell culture medium comprising about 2% v/v human serum albumin;
   (iv) further culturing the cells for between 24 hours and 36 hours in the second cell culture medium; and
   (v) harvesting said cells for use in said allogeneic therapy.

2. The method of claim 1, wherein the mesenchymal stromal cell is a mesenchymal progenitor cell (MPC).

3. The method of claim 1, wherein the sample of cells in step (i) comprises between $1.0 \times 10^3$ cells per cm$^2$ of culture vessel and $1.0 \times 10^{10}$ cells per cm$^2$ of culture vessel.

4. The method of claim 1, wherein the sample of cells in step (i) comprises between $1.0 \times 10^3$ cells per cm$^2$ of culture vessel and $1.0 \times 10^7$ cells per cm$^2$ of culture vessel.

5. The method of claim 1, wherein the sample of cells in step (i) are cultured until said cells are approximately 85% confluent.

6. The method of claim 1, wherein the second cell culture medium is phenol red-free.

* * * * *